United States Patent
Gao et al.

(10) Patent No.: US 11,242,520 B2
(45) Date of Patent: Feb. 8, 2022

(54) METHOD FOR NON-INVASIVE PRENATAL DIAGNOSIS BASED ON EXOSOMAL DNA AND APPLICATION THEREOF

(71) Applicants: BGI Shenzhen, Shenzhen (CN); MGI Tech Co., Ltd., Shenzhen (CN)

(72) Inventors: Ya Gao, Shenzhen (CN); Sen Lu, Shenzhen (CN); Jia Zhao, Shenzhen (CN); Peng Zeng, Shenzhen (CN); Fang Chen, Shenzhen (CN); Hui Jiang, Shenzhen (CN)

(73) Assignees: BGI SHENZHEN, Shenzhen (CN); MGI TECH CO., LTD., Shenzhen (CN)

( * ) Notice: Subject to any disclaimer, the term of this patent is extended or adjusted under 35 U.S.C. 154(b) by 243 days.

(21) Appl. No.: 16/519,671

(22) Filed: Jul. 23, 2019

(65) Prior Publication Data
US 2019/0345482 A1 Nov. 14, 2019

Related U.S. Application Data

(63) Continuation of application No. PCT/CN2017/072488, filed on Jan. 24, 2017.

(51) Int. Cl.
*C12Q 1/6806* (2018.01)
*C12N 15/10* (2006.01)
*G01N 35/00* (2006.01)

(52) U.S. Cl.
CPC ....... *C12N 15/1013* (2013.01); *C12Q 1/6806* (2013.01); *G01N 35/0098* (2013.01)

(58) Field of Classification Search
CPC .... C12Q 1/6806; C12Q 1/6883; C12N 15/10; C12N 15/1013; G01N 33/53; G01N 35/0098; C12M 1/34
See application file for complete search history.

(56) References Cited

U.S. PATENT DOCUMENTS

2013/0230858 A1* 9/2013 Cantor ................. C12Q 1/6804
435/6.12

FOREIGN PATENT DOCUMENTS

| CN | 103403183 B | 10/2014 |
|---|---|---|
| CN | 105400864 A | 3/2016 |
| CN | 105779586 A | 7/2016 |
| WO | 2009147519 A1 | 12/2009 |
| WO | 2012087241 A1 | 6/2012 |
| WO | 2014028862 A1 | 2/2014 |
| WO | 2015153732 A2 | 10/2015 |

OTHER PUBLICATIONS

Kahlert et al. Identification of double-stranded genomic DNA spanning all chromosomes with mutated KRAS and p53 DNA in the serum exosomes of patients with pancreatic cancer. J. Biol. Chem. (2014) vol. 289, No. 7, pp. 3869-3875.*
Mitchell, M.D., et al. "Placental exosomes in normal and complicated pregnancy" Oct. 2015, American Journal of Obstetrics & Gynecology, S173-S181.
Tannetta, D., et al. "Update of syncytiotrophoblast derived extracellular vesicles in normal pregnancy and preeclampsia" Journal of Reproductive Immunology 119 (2017) 98-106.
Allenson, K., et al "High prevalence of mutant KRAS in circulating exosome-derived DNA from early-stage pancreatic cancer patients" Annals of Oncology, vol. 28, Issue 4 (2017) 741-747.
Ko, J. et al "Detection and isolation of circulating exosomes and microvesicles for cancer monitoring and diagnostics using micro-/nano-based devices" Analyst (2016) 141, 450-460.
Contreras-Naranjo, J.C., et al. "Microfluidics for exosome isolation and analysis:enabling liquid biopsy for personalized medicine" Lab Chip. (2017) 17(21), 3558-3577.
Tong, M., Chamley, L.W., "Placental Extracellular Vesicles and Feto-Maternal Communication" Cold Spring Harb Perspect Med. (2015) 5(3), 1-17.
Keller, S., et al. "Body fluid derived exosomes as a novel template for clinical diagnostics" Journal of Translational Medicine (2011) 9:86, 1-9.
Wang, L., et al. "Exosomal double-stranded DNA as a biomarker for the diagnosis and preoperative assessment of pheochromocytoma and paraganglioma" Molecular Cancer (2018) 17:128, 1-6.
Office Action issued for EP application 17893815.5, dated Dec. 11, 2019.
Sabapatha, A. et al., "Specific isolation of placenta-derived exosomes from the circulation of pregnant women and their immunoregulatory consequences", American Journal of Reproductive Immunology, 56(5-6), Oct. 31, 2006 (Oct. 31, 2006), ISSN: 1046-7408, see pp. 345-355.
International Search Report issued for PCT/CN2017/072488, dated Oct. 25, 2017.
Written Opinion of the International Searching Authority issued for PCT/CN2017/072488, dated Oct. 25, 2017.

* cited by examiner

*Primary Examiner* — David C Thomas
(74) *Attorney, Agent, or Firm* — Westman, Champlin & Koehler, P.A.; Z. Peter Sawicki; Amanda M. Prose

(57) ABSTRACT

Provided is a method for isolating exosomal DNA, the method comprising: (i) providing a sample, wherein the sample comprises a blood sample from peripheral blood of a pregnant woman; and (ii) subjecting the sample to isolating, thus obtaining the exosomal DNA. Also provided are a method for detecting a blood sample, a method for constructing a sequencing library on a blood sample, a method for high-throughput sequencing an exosomal DNA sequencing library, a method for non-invasive prenatal gene detection, a device for non-invasive prenatal gene detection, and a kit for detecting a blood sample and use thereof.

18 Claims, 1 Drawing Sheet

METHOD FOR NON-INVASIVE PRENATAL DIAGNOSIS BASED ON EXOSOMAL DNA AND APPLICATION THEREOF

CROSS-REFERENCE TO RELATED APPLICATIONS

This application is a U.S. continuation application based upon PCT Application No. PCT/CN2017/072488, filed with the China National Intellectual Property Administration on Jan. 24, 2017, and published as WO2018/137141 on Aug. 2, 2018, the entire content of which is incorporated herein by reference.

FIELD

The present disclosure relates to the field of detection, in particular to a method for non-invasive prenatal diagnosis based on exosomal DNA.

BACKGROUND

The fact that cell-free fetal DNA (cf-fDNA) is present in maternal blood, first proven in 1997, has opened a new chapter in prenatal genetic diagnosis.

In recent years, with the discovery of cell-free fetal DNA in maternal blood and the development of high-throughput sequencing technology, a new non-invasive prenatal screening technology based on sequencing free DNA in plasma of a pregnant woman has been applied to clinical application, which can detect common chromosome aneuploidy in fetus in a more accurate and effective way than traditional serological screening method.

So far, the cf-fDNA has been widely applied in non-invasive prenatal detection, including determination of fetal sex, autosomal genetic disease (such as β thalassemia, achondroplasia), RhD blood type, genetic disease (including aneuploidy such as trisomy 21 syndrome, sex chromosome-linked disease such as X-linked hemophilia and fragile X syndrome, and the like).

Current research indicates that the cell-free DNA (cfDNA) in plasma of a pregnant woman is an extracellular small-fragment DNA which is free in blood circulation of the pregnant woman, and it is mainly originated from apoptotic placental chorionic cells and enters the maternal blood circulation via penetrating through placental barrier.

The biological basis of this non-invasive prenatal detection technique lies on that genomic DNA originated from the placental trophoblast cells during pregnancy is degraded into a DNA fragment of about 170 bp, which enters the maternal blood circulation through maternal-fetal interface and thus can be detected in the peripheral blood, with a role similar with chorionic villus sampling. Whereas, it is still unclear how the genomic DNA of the placental trophoblast cell is degraded into DNA fragments, by which mechanism the DNA fragment is released into the maternal circulation, and whether the degraded DNA fragment exhibits regulatory effect on the pregnancy process. Besides, the total cell-free DNA in peripheral blood of a pregnant woman is a mixture of maternal-derived and fetal-derived free DNAs, with the fetal-derived free DNA only accounting for about 10% of the total free DNA on average (even lower in early pregnancy), despite its content increases as the gestational weeks. At present, the maternal-derived free DNA and the fetal-derived free DNA cannot be distinguished by most of high-throughput sequencing methods due to genetic similarity, which brings a great technical difficulty for accurate non-invasive prenatal detection.

For example, the existing method for detecting chromosomal aneuploidy based on cell-free DNA in plasma has problems of 1) an unclear source for the cell-free DNA in plasma, and 2) a low concentration of fetal-derived free DNA in plasma (resulting in the fact that the aneuploidy in the plasma fetal-derived free DNA is undetectable for a sample in early pregnancy) and a large difference in samples.

Therefore, there is an urgent need in the art to develop a new method of non-invasive prenatal diagnosis with high accuracy and sensitivity.

SUMMARY

An object of the present disclosure is to provide a method for non-invasive prenatal diagnosis with high accuracy and sensitivity.

In a first aspect, provided in embodiments is a method for isolating exosomal DNA, including:
  (i) providing a sample, wherein the sample includes a blood sample from peripheral blood of a pregnant woman); and
  (ii) subjecting the sample to isolating, thus obtaining the exosomal DNA.

In another preferred embodiment, the exosomal DNA includes fetal-derived DNA.

In another preferred embodiment, the isolating further includes of:
  (ii-a) isolating exosomes from the blood sample; and
  (ii-b) extracting DNA from the isolated exosomes.

In a further preferred embodiment, the blood sample is selected from the group consisting of plasma, serum and a combination thereof.

In a further preferred embodiment, the blood sample is a pretreated blood sample.

In a further preferred embodiment, the blood sample is a supernatant after centrifugation.

In a still further preferred embodiment, the supernatant is obtained by two steps:
  (a) collecting the blood sample with a collection device, wherein the collection device contains an anticoagulant, and
  (b) centrifuging the collection device containing the blood sample at high speed to obtain the supernatant.

In a still further preferred embodiment, the isolating is conducted by using a magnetic-bead separation method, an affinity separation method or a combination thereof.

In a furthermore preferred embodiment, the isolating is conducted by sorting or capturing with a specific antibody against at least one of antigens of PLAP, CD9, CD63 and CD81.

In a furthermore preferred embodiment, the magnetic-bead separation method is conducted by isolating with a magnetic bead conjugated with a CD9 antibody or a PLAPl antibody on the surface.

In a second aspect, provided in embodiments is a method for detecting a blood sample, including:
  (a) performing the method described in the first aspect to obtain exosomal DNA; and
  (b) detecting the presence of fetal-derived DNA in the exosomal DNA.

In another preferred embodiment, in (b), the presence of fetal-derived DNA in the exosomal DNA is detected by at least one of techniques selected from PCR amplification technique, sequence-specific probe capturing technology and high-throughput sequencing technology.

In a further preferred embodiment, the detecting includes determining the number and/or sequence information of fetal-derived Y chromosomes.

In a still further preferred embodiment, the detecting includes determining the number and/or sequence information of fetal-derived X chromosomes.

In a furthermore preferred embodiment, the detecting includes determining the number and/or sequence information of fetal-derived autosomes.

In a furthermore preferred embodiment, the detecting includes determining the fetal-derived DNA fraction.

In a third aspect, provided in embodiments is a method for constructing a sequencing library on a blood sample, including:
(a) performing the method described in the first aspect to obtain exosomal DNA; and
(b) constructing a sequencing library for the exosomal DNA to obtain an exosomal DNA sequencing library.

In a fourth aspect, provided in embodiments is a method for high-throughput sequencing an exosomal DNA sequencing library, including:
(a) performing the method described in the third aspect to obtain the exosomal DNA sequencing library; and
(b) subjecting the exosomal DNA sequencing library to high-throughput sequencing to obtain information of the exosomal DNA.

In a fifth aspect, provided in embodiments is a method for non-invasive prenatal gene detection, including:
(a) performing the method described in the first aspect to obtain exosomal DNA;
(b) detecting the presence of fetal-derived DNA in the exosomal DNA; and
(c) generating a gene detection result based on information obtained in (b).

In a sixth aspect, provided in embodiments is a method for non-invasive prenatal gene detection, including:
(a) performing the method described in the fourth aspect to obtain information of exosomal DNA; and
(b) generating a gene detection result based on the information obtained in (a),
wherein the exosomal DNA includes fetal-derived DNA.

In another preferred embodiment, the gene detection includes: determination of fetal-derived DNA fraction, determination of fetal sex, detection of autosomal genetic disease, detection of sex chromosome-linked disease, determination of RhD blood type or detection of chromosome aneuploidy.

In a further preferred embodiment, the detection of chromosomal aneuploidy includes detection of trisomy 21, trisomy 18 or trisomy 13.

In a still further preferred embodiment, the method in any aspect described above is non-diagnostic and non-therapeutic.

In a seventh aspect, provided in embodiments is a device for non-invasive prenatal gene detection, including:
an isolation device, configured to perform the method describe in the first aspect so as to obtain exosomal DNA;
a detection device, connected to the isolation device and configured to detect the presence of fetal-derived DNA in the exosomal DNA; and
an output device, connected to the detection device and configured to generate a gene detection result based on information obtained by the detection device.

In an eighth aspect, provided in embodiments is a kit for detecting a blood sample, including:
(a) a capture agent for capturing exosomes, configured to capture exosomes in a blood sample from peripheral blood of a pregnant woman, wherein the exosomes include fetal-derived exosomal DNA;
(b) an extractant for extracting DNA from the exosomes captured in (a); and
(c) an instruction for use, configured to indicate the isolation of exosomal DNA in the blood sample from the peripheral blood of the pregnant woman and the detection of the exosomal DNA isolated.

In another preferred embodiment, the capture agent includes: (a) a specific antibody against at least one of antigens of PLAP, CD9, CD63 and CD81; or (b) magnetic beads conjugated with the antibody.

In a ninth aspect, provided in embodiments is use of the kit described in the eighth aspect in preparing a kit for non-invasive prenatal diagnosis.

In another preferred embodiment, the prenatal diagnosis includes: determination of fetal sex, detection of autosomal genetic disease, detection of sex chromosome-linked disease, determination of RhD blood type, or detection of chromosome aneuploidy.

In a further preferred embodiment, the detection of chromosomal aneuploidy includes detection of trisomy 21, trisomy 18 or trisomy 13.

It should be understood, regarding the scope of the present disclosure, various technical features of the present disclosure described as above and various technical features specifically described as below (like in embodiments) may be combined with each other to constitute a new and preferred technical solution, which will not be repeated due to limited space.

DETAILED DESCRIPTION

Figure 1:
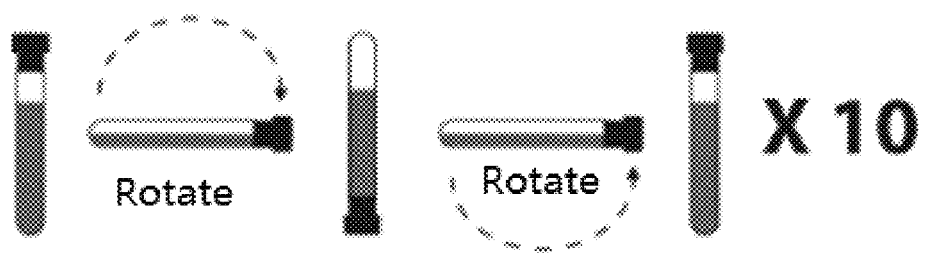
FIG. 1 is a schematic diagram showing mixing by rotation.

The present disclosure is accomplished by present inventors based on the findings: the present inventors after extensive and intensive researches, have unexpectedly discovered for the first time that exosomes in plasma of a pregnant woman during pregnancy comprise DNA fragments and that such the exosomal DNA contains quite rich fetal-derived DNA, thus suggesting that accurate and specific information useful in prenatal diagnosis can be provided through isolating or enriching the fetal-derived DNA or total exosomal DNA containing the fetal-derived DNA. Specifically, determination of fetal-derived DNA fraction, fetal sex, autosomal genetic disease, sex chromosome-linked disease, RhD blood type and chromosomal aneuploidy can be provided accurately via high-throughput sequencing the fetal-derived DNA present in the total exosomes during pregnancy, and whole genomics sequences information can be further provided.

Exosome

As used herein, the term "exosome" or "exosomes" are small vesicles in a diameter of about 40 to 120 nm and a density of about 1.13 to 1.19 g/ml secreted by late endosomes in living cells, which contain endosomal protein markers (such as TSG101, CD9, CD63, CD81 and the like) on the surface of lipid membrane. The exosomes are commonly present in body fluid, also can be found in blood, urine, amniotic fluid and malignant tumor-caused ascites.

The change of exosome content during pregnancy is related to gestational weeks, and the exosome content in peripheral blood of a normal pregnant woman during pregnancy is significantly increased by about 20 to 50 times compared with a non-pregnant woman, with increase of the exosome content as the gestational weeks. The fetal-derived exosomes in peripheral blood of a pregnant woman are detectable in gestational weeks 5 to 6 through quantification of PLAP on the surface of the fetal-derived exosomes, and its content increases rapidly as the gestational weeks, suggesting an increased release of placental-specific exosomes into maternal circulation with maturation of the placenta and active maternal-fetal exchange. Currently, exosomes containing fetal-derived DNA have not been found by scientific researchers.

The present disclosure is accomplished by the present inventors based on the findings: some exosomes are released by human placental trophoblast cells and enter the maternal circulation during pregnancy, and parts of the exosomes contain fetal-derived DNA which is useful in prenatal diagnosis of fetus, for example as a molecular marker for chromosomal abnormality. It is indicated by the research of the present disclosure that fetal-derived DNA contained in exosomes during pregnancy can be used for detection of DNA which covers the whole genomic level.

Due to the similarity of fetal-derived DNA contained in exosomes and cell-free DNA (cfDNA) in plasma, the fetal-derived DNA contained in exosomes can be used as a marker for fetal DNA molecules which is similar with the plasma cfDNA. Further, the placental-specific exosome may become a new candidate molecule for studying disease occurrence, development, early prediction, pathological classification, prognosis and therapeutic target during pregnancy, demonstrating a favorable application prospect.

In a specific embodiment of the present disclosure, it is found for the first time that fetal sex and chromosomal aneuploidy can be accurately determined by high-throughput sequencing fetal-derived DNA which is present in exosomes during pregnancy. For one typical method, exosomes are isolated by combination of SBI exoquick with CD9/PLAP immunomagnetic beads (Thermofish), the exosomal DNA is extracted for high-throughput sequencing, so as to detect fetal sex and aneuploidy (such as trisomy 21), in which the exosomal DNA contains plenty of fetal-derived DNAs.

Capture Agent or Sorting Agent

As used herein, the terms "capture agent" and "sorting agent" are used interchangeably and refer to agents that can capture, enrich or sort exosomes from a blood sample or a body fluid sample.

A typical capture agent includes: (a) a specific antibody against at least one of antigens of PLAP, CD9, CD63 and CD81; or (b) magnetic beads conjugated with the antibody. For example, Exoquick solution and/or immunomagnetic beads capable of specifically recognizing CD9 and/or placental alkaline phosphatase (i.e. PLAP) can be employed.

The immunomagnetic beads are spherical magnetic particles which are conjugated with monoclonal antibodies on their surfaces, and specifically capture total exosomes or fetal-derived exosomes in plasma through the interaction between the monoclonal antibody and antigens (such as CD9, CD63, CD81 and PLAP) located on the surfaces of exosomes.

Total exosomes can be isolated by methods including a precipitation and centrifugation method (SBI company), and immunomagnetic beads separation (Thermo Fisher company), which can be combined together with the advantages of obtaining a great number of exosomes by using the reagent from SBI, and overcoming the deficiency of low purity (for the exosomes obtained by SBI company) through the immunomagnetic beads separation.

After isolation, the exosomal DNA was extracted for routine library construction and high-throughput sequencing. The fetal sex and fetal-derived DNA fraction were determined according to the number and/or sequences information of Y chromosomes. The detection of RhD blood type, autosomal genetic disease, sex chromosome-linked disease and chromosome aneuploidy was conducted by statistical analysis according to the sequences information of each chromosome.

It should be noted that the total exosomal DNA extracted from peripheral blood of a pregnant woman includes both maternal-derived DNA and fetal-derived DNA. "Fetal-derived DNA fraction" as used herein refers to the ratio of the number of fetal-derived DNA molecules to the number of total exosomal DNA molecules.

Mechanism

In order to understand the present disclosure easily, the mechanism is provided as below for reference. It should be appreciated that the protection scope of the present disclosure is not limited by the mechanism.

The present inventors propose a scientific mechanism and explanation as below. Exosomes released from placental trophoblast cells are found to be present in maternal blood during pregnancy, which contain cell-free fetal DNA and thus is more suitable as a molecular marker for detection of fetal chromosomal abnormality through high-throughput sequencing compared to plasma cell-free DNA derived from both mother and fetus.

Specifically, maternal-derived and fetal-derived exosomes are present in maternal blood during pregnancy, while exosomes derived from lymphocyte can be extracted from peripheral blood of a non-pregnant woman by chromatographic analysis and immunoadsorption. Further, not only maternal-derived exosomes but also fetal-derived exosomes have been detected in peripheral blood of a pregnant woman through quantifying with a placental-specific PLAP antibody. Thus, it demonstrates that the exosomes present in maternal blood during pregnancy are derived from both mother and fetus, which is similar with the plasma cell-free DNA derived from both mother and fetus in a pregnant woman.

It has been proved by in vitro and in vivo experiments that the fetal-derived exosomes in maternal blood are mainly generated in placental trophoblast cells and then released into maternal blood. In the placental trophoblast cells, primary endosomes develop into mature endosomes through invagination of cell membranes, subsequently some mature endosomes enter lysosome but some endosomes form exosomes along with plenty of signal molecules (such as miRNA, protein and the like) via encapsulation which are subsequently released into extracellular matrix through membrane fusion and then into maternal blood.

Despite unclear biosynthesis, transportation, inclusion encapsulation and efficacy of exosome, it is suggested by the present findings that the fetal-derived exosomes can involve in regulation of some important processes during pregnancy, such as immune tolerance, maternal-fetal interface remodeling, inflammatory response and the like by actively phagocytizing tissue-specific inclusions and releasing them into the maternal circulation. In addition, the exosomes have a stable bilayer lipid membrane, which seems to be more helpful in maintaining the stability of fetal-derived DNA.

Method for Detecting Fetal DNA Based on Exosome in Peripheral Blood of Pregnant Woman The present disclosure provides a method for detecting fetal DNA based on exosomes in peripheral blood of a pregnant woman, where the method may be diagnostic and may be non-diagnostic.

Typically, the method of the present disclosure includes steps of:
(a) providing a blood sample, wherein the blood sample is selected from blood, plasma, serum and a combination thereof from peripheral blood of a pregnant woman;
(b) isolating exosomes from the blood sample, wherein the exosomes include fetal-derived exosomes;
(c) extracting DNA from the isolated exosomes, wherein the DNA extracted contains fetal-derived DNA; and
(d) detecting the DNA extracted in step (c) by performing such as PCR amplification or sequencing, so as to obtain a corresponding analysis result or detection result.

In the method of the present disclosure, peripheral blood of a pregnant woman can be collected with a conventional method, and then plasma or serum in the peripheral blood is separated. For example, the peripheral blood (e.g., in a volume of about 2 to 20 ml, more preferably 3 to 10 ml) is collected by using a commercially available Streck tube. Plasma or serum can be separated by using a two-step method.

For the plasma or serum separated, the total exosomes can be isolated by centrifugation or the like. Preferably, the exosomes which contain fetal-derived DNA, among the total exosomes obtained, may be further enriched or captured, for example, with magnetic beads conjugated with CD9/PLAP antibody through the magnetic-beads separation method.

For the total exosomes or fetal-derived exosomes isolated, DNA in the exosomes may be extracted, thus fetal-derived DNA can be detected. For example, the fetal-derived DNA can be subjected to a high-throughput sequencing library construction firstly, followed by sequencing and analyzing, so as to detect fetal sex, Rh blood type, chromosome aneuploidy, genetic abnormality and the like.

In another preferred embodiment, a typical method of the present disclosure includes steps as below.

Step 1: Plasma exosomes are isolated from a blood sample with known methods or reagents, such as the commercially available SBI quick reagent from SBI Company.

Step 2: Fetal-derived plasma exosomes are enriched or captured from the plasma exosomes obtained in step 1. For example, after dissolved in a PBS buffer, the exosome precipitate generated in step 1 is captured or enriched with the CD9/PLAP immunomagnetic beads, followed by incubating at a temperature (e.g., 4 to 8° C.) for a time period (e.g., 2 to 24 hours, or overnight), thus obtaining a magnetic bead-exosome binary complex. The CD9/PLAP immunomagnetic beads can be prepared by conventional methods or are commercially available (for example, CD9/PLAP immunomagnetic beads purchased from Thermo Fisher).

Step 3: DNA is extracted from the magnetic bead-exosome binary complex obtained in step 2, followed by library constructing (with increased PCR cycles) and/or sequencing, so as to obtain sequencing data.

Step 4: The sequencing data is subjected to information analysis, thus obtaining corresponding analysis results, including for example the fetal-derived DNA fraction, fetal sex, RhD blood type, presence or absence of chromosomal aneuploidy, autosomal genetic disease and sex chromosome-linked disease and the like for the sample to be detected.

The present disclosure mainly includes the following advantages.
(a) The present disclosure provides a method for non-invasive prenatal diagnosis, which is more accurate and specific than the existing methods.
(b) The method of the present disclosure is based on exosomal DNA in plasma of a pregnant woman, with a definite source and more stable quality.
(c) The method of the present disclosure can be combined with other detection techniques in a more convenient way, such that for example the RNA, protein, metabolic product and the like which are easily to be degraded in plasma can be simultaneously detected.

The present disclosure is further illustrated as below in combination with specific examples. It is to be understood that the examples are not intended to limit the scope of the disclosure. Experimental methods in the examples in which the specific conditions are not indicated are generally conducted in accordance with conventional conditions, for example, the conditions described in Sambrook et al. (Molecular Cloning: Laboratory Manual, New York: Cold Spring Harbor Laboratory Press, 1989) or in accordance with the conditions instructed by a manufacturer. Percentage and parts are by weight unless otherwise stated.

EXAMPLE 1

Fetal Sex Determination and Chromosome Aneuploidy Detection Based on Plasma Exosomes in Pregnant Woman 1.1 Plasma Separation with a Two-Step Method
1.1.1 Streck Cell-Free DNA BCT Sampling 10 mL peripheral blood from a pregnant woman or a normal person was sampled according to standard peripheral blood collection operation, after which the blood collection tube was immediately rotated for 10 times slowly to mix the blood sample with a component in the tube (refer to FIG. 1), with the blood collection tube stood uprightly on a tube holder at room temperature (6-35° C.). Note that delaying the time for rotation may result in failure of detection.

1.1.2. Plasma Separation 1.1.2.1 The blood collection tube containing the blood sample was centrifuged at 1600 g and 4° C. for 10 minutes, and the supernatant obtained was dispensed into multiple centrifuge tubes in 2.0 mL on the ice.

1.1.2.2 The centrifuge tubes were centrifuged at 16000 g and 4° C. for 10 minutes, and the supernatant obtained (i.e. plasma) was transferred into new numbered centrifuge tubes in 2.0 mL on the ice, with 600 μL plasma per tube.

1.1.2.3 The plasma samples obtained were immediately stored at a low temperature, with storage in a refrigerator at −20° C. for use within one week and storage in a refrigerator at −80° C. for a long-term period.

Isolation of Total Exosomes Containing Fetal-Derived Exosomes

Samples used in 1.2 are plasma samples derived from 2 normal males, 2 pregnant women with normal male fetus, 2 pregnant women with normal female fetus, 4 pregnant women with fetus suffering from trisomy 21 (two male fetuses and two female fetuses respectively) and 2 pregnant women with fetus suffering from trisomy 18 (one male fetus and one female fetus) which were obtained by the step of plasma separation in 1.1.2, in which the information on fetal sex and chromosomal aneuploidy of the plasma samples has been acquired by existing detection techniques.

1.2.1 Separation of Plasma Exosomes with ExoQuick Exosome Precipitation Solution Reagent From SBI System Biosciences 1.2.1.1 63 μl of ExoQuick Exosome Precipitation Solution reagent was added into 250 μL of plasma sample, with pipetting up and down for fully mixing, and placed in an ice bath for 30 minutes.

1.2.1.2 The plasma sample was centrifuged at 1500 g for 30 minutes, followed by removing the supernatant (named as SBI supernatant).

1.2.1.3 The precipitate obtained in step 1.2.1.2 was centrifuged at 1500 g for 5 minutes, and the trace of supernatant was carefully removed.

1.2.1.4 The precipitate obtained in step 2.1.3 was dissolved in 100 μL of the PBS buffer at 37° C.

1.2.2 Separation of Exosomes With Exosome-Human CD9 Magnetic Beads From Thermo Fisher 1.2.2.1 The magnetic beads conjugated with CD9 antibody were sharked for 30 seconds for fully mixing.

1.2.2.2 500 μL of a separation buffer (containing PBS and 0.1% BSA) was added into 40 μL magnetic beads, with pipetting up and down for mixing, followed by centrifuging at 3000 g for 5 seconds and placing onto a magnetic separator for 2 minutes, with the supernatant removed.

1.2.2.3 100 μL of PBS buffer containing exosomes obtained in step 1.2.1.4 was added into the magnetic beads in step 1.2.2.2, with pipetting up and down for mixing, and incubated in a rotary shaker at 4° C. overnight (i.e. 18 to 22 hours).

1.2.2.4 After centrifugation of the mixture of magnetic beads and exosomes obtained in step 1.2.2.3 for 5 seconds, 500 μL of the separation buffer was added and the mixture was stood onto the magnetic separator for 2 minutes, with the supernatant removed.

1.2.2.5 Another 500 μL of the separation buffer was added and the mixture was stood onto the magnetic separator for 2 minutes, with the supernatant removed.

1.3 Total Exosomal DNA Extraction, Library Construction and High-Throughput Sequencing 1.3.1 Exosomal DNA Extraction Exosomal DNA was extracted by using the Magen MagPure Circulating DNA Mini KF Kit.

1.3.2 The exosomal DNA extracted was subjected to library constructing and high-throughput sequencing in accordance with methods in a patent application (application name: Method of constructing a sequencing library based on blood sample and use of determining fetal genetic abnormality; and publication No.: CN105400864 A). All the steps and parameters were same to those in the patent application except for 19 of PCR cycles for library construction.

1.3.3 Sequencing data analysis, fetal sex determination and chromosome aneuploidy detection were conducted in accordance with methods in a patent application (application name: non-invasive detection of fetal genetic abnormality; and publication No.: CN103403183 B).

Table 1 shows the detection results, which indicate correct detection of fetal sex for all samples, correct detection of trisomy 21 for 4 samples and correct detection of trisomy 18 for 2 samples. The results obtained are identical to the pre-know clinical information of corresponding plasma samples which has been acquired by existing detection techniques.

TABLE 1

| Sample No. | Sequencing data (M) | Effective data (M) | Unique mapping rate | Repetition rate | Fetal sex | Chr13 | chr18 | chr21 |
| --- | --- | --- | --- | --- | --- | --- | --- | --- |
| 1-1 | 6.36 | 4.48 | 0.72 | 0.03 | XY | normal | normal | T21 |
| 1-2 | 8.29 | 4.85 | 0.71 | 0.22 | XY | normal | normal | T21 |
| 1-3 | 14.42 | 6.70 | 0.62 | 0.27 | XY | normal | normal | T21 |
| 2-1 | 6.89 | 4.91 | 0.72 | 0.01 | XY | normal | normal | T21 |
| 2-2 | 9.00 | 6.05 | 0.71 | 0.08 | XY | normal | normal | T21 |
| 2-3 | 13.74 | 6.31 | 0.66 | 0.33 | XY | normal | normal | T21 |
| 3-1 | 6.80 | 4.97 | 0.74 | 0.01 | XX | normal | normal | T21 |
| 3-2 | 6.34 | 4.25 | 0.71 | 0.07 | XX | normal | normal | T21 |
| 3-3 | 14.75 | 9.45 | 0.69 | 0.10 | XX | normal | normal | T21 |
| 4-1 | 10.11 | 7.29 | 0.73 | 0.01 | XX | normal | normal | T21 |
| 4-2 | 9.22 | 5.91 | 0.71 | 0.13 | XX | normal | normal | T21 |
| 4-3 | 17.13 | 9.76 | 0.67 | 0.19 | XX | normal | normal | T21 |
| 5-1 | 5.72 | 4.08 | 0.72 | 0.02 | XX | normal | T18 | normal |
| 5-2 | 9.22 | 6.30 | 0.72 | 0.06 | XX | normal | T18 | normal |
| 5-3 | 11.49 | 5.51 | 0.67 | 0.32 | XX | normal | T18 | normal |
| 6-1 | 6.79 | 4.86 | 0.72 | 0.01 | XY | normal | T18 | normal |
| 6-2 | 8.58 | 5.97 | 0.71 | 0.03 | XY | normal | T18 | normal |
| 6-3 | 14.80 | 7.83 | 0.69 | 0.28 | XY | normal | T18 | normal |
| 7-1 | 8.16 | 5.86 | 0.73 | 0.01 | XY | normal | normal | normal |
| 7-2 | 12.96 | 8.99 | 0.71 | 0.03 | XY | normal | normal | normal |
| 7-3 | 12.90 | 7.00 | 0.67 | 0.22 | XY | normal | normal | normal |
| 8-1 | 7.63 | 5.38 | 0.71 | 0.01 | XY | normal | normal | normal |
| 8-2 | 6.40 | 4.38 | 0.71 | 0.04 | XY | normal | normal | normal |
| 8-3 | 10.80 | 6.31 | 0.71 | 0.22 | XY | normal | normal | normal |
| 9-1 | 5.89 | 4.09 | 0.72 | 0.06 | XX | normal | normal | normal |
| 9-2 | 8.45 | 5.38 | 0.70 | 0.13 | XX | normal | normal | normal |
| 9-3 | 13.47 | 7.50 | 0.70 | 0.26 | XX | normal | normal | normal |
| 10-1 | 5.30 | 3.75 | 0.71 | 0.01 | XX | normal | normal | normal |
| 10-2 | 7.83 | 5.41 | 0.71 | 0.04 | XX | normal | normal | normal |
| 10-3 | 19.15 | 11.82 | 0.71 | 0.17 | XX | normal | normal | normal |

TABLE 1-continued

| Sample No. | Sequencing data (M) | Effective data (M) | Unique mapping rate | Repetition rate | Fetal sex | Chr13 | chr18 | chr21 |
|---|---|---|---|---|---|---|---|---|
| 11-3 | 12.81 | 6.12 | 0.67 | 0.32 | XY | normal | normal | normal |
| 12-3 | 8.96 | 2.88 | 0.48 | 0.26 | XY | normal | normal | normal |

Note 1:
For each sample, number -1 means plasma; number -2 means SBI supernatant (i.e. a mixture of all components in plasma except for exosomes); number -3 means exosomal DNA.
Note 2:
samples in Nos. 1-4 mean trisomy 21 samples; samples in Nos. 5-6 mean trisomy 18 samples; samples in Nos. 7-8 mean normal male-fetus samples; samples in Nos. 9-10 mean normal female-fetus samples; and samples in Nos. 11-12 mean normal male samples.

EXAMPLE 2

Fetal Sex Determination Based on Plasma Exosomes in Pregnant Woman 2.1 Plasma SEPARATION WITH a Two-Step Method
The plasma was separated by the method in 1.1.
2.2 Isolation of Fetal-Derived Exosomes
The fetal-derived exosomes in plasma were isolated by the steps in 1.1.2 except that the magnetic beads conjugated with CD9 antibody were replaced with magnetic beads conjugated with PLAP antibody.
2.3 The fetal-derived exosomal DNA extraction, library construction and high-throughput sequencing were conducted according to the methods in 1.3.

Table 2 shows the detection results, which indicate correct detection of fetal sex for all samples, with results identical to those detected with the plasma cell-free DNA (cfDNA) in the existing method for fetal sex determination.

TABLE 2

| Sample No. | sequencing data (M) | Effective data (M) | Unique mapping rate | Repetition rate | Fetal sex |
|---|---|---|---|---|---|
| PLAP-1 | 58.3 | 24.3 | 0.62 | 0.13 | XY |
| PLAP-2 | 32.7 | 14.7 | 0.58 | 0.07 | XY |
| PLAP-3 | 15.0 | 2.75 | 0.41 | 0.38 | XY |
| PLAP-4 | 7.99 | 1.22 | 0.42 | 0.49 | XY |
| PLAP-5 | 11.3 | 2.22 | 0.53 | 0.48 | XY |
| PLAP-6 | 16.1 | 4.17 | 0.55 | 0.35 | XY |
| PLAP-7 | 18.8 | 5.12 | 0.56 | 0.33 | XY |

Note:
PLAP-1 and -2 are samples conducted in a first batch; PLAP-3, -4, -5, -6 and -7 are samples conducted in a second batch.

Example 3

Assay of Fetal-Derived Exosomes With Western Blot Analysis

Figure 2:
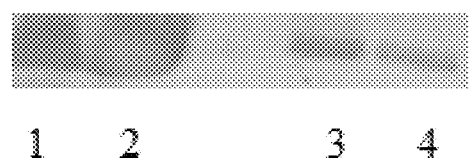
FIG. 2 is a schematic diagram showing Western Blot results, in which Lanes 1 and 2 are Western Blot results of total plasma exosomes isolated with ExoQuick Exosome Precipitation Solution and a PLAP antibody; and Lanes 3 and 4 are respectively a Western Blot result of total plasma exosomes and a CD9 magnetic bead or a PLAP magnetic bead.

The total plasma exosomes isolated with ExoQuick Exosome Precipitation Solution in Example 1 and the exosomes isolated with CD9/PLAP magnetic beads were assayed with the Western Blot method, with results shown in FIG. 2.

FIG. 2 shows the results, which indicate the total plasma exosomes isolated with the ExoQuick Exosome Precipitation Solution and the exosomes isolated with CD9/PLAP magnetic beads both contain plenty of PLAP proteins, suggesting successful isolation of fetal-derived exosomes.
Other Exosomes Separation Methods Except for the polymer precipitation (i.e. SBI Exoquick) and the CD9/PLAP immunomagnetic beads involved in the present disclosure, exosomes can be isolated by using other methods, such as ultracentrifugation, density gradient centrifugation and the like. All the methods described above are capable of isolating exosome theoretically and the DNA extracted from the exosome obtained can be subjected to high-throughput sequencing.

All the documents cited in the present disclosure are incorporated herein in their entireties by reference, as if each document is cited separately as a reference. In addition, it should be appreciated that the skilled in the art can make various modifications and changes after reading the teachings of the present disclosure, and such the equivalent form is also fallen into the scope of the present appended claims.

What is claimed is:

1. A method for detecting fetal-derived DNA in a blood sample, comprising:
   (i) providing a sample, wherein the sample comprises a blood sample from peripheral blood of a pregnant woman;
   (ii) subjecting the sample to an isolating step to obtain exosomal DNA, wherein the exosomal DNA comprises fetal-derived DNA; and
   (iii) detecting the presence of the fetal-derived DNA in the exosomal DNA.

2. The method according to claim 1, wherein the isolating step (ii) further comprises:
   (ii-a) isolating exosomes from the blood sample; and
   (ii-b) extracting DNA from the isolated exosomes.

3. The method according to claim 1, wherein the blood sample is selected from the group consisting of plasma, serum and a combination thereof.

4. The method according to claim 1, wherein the blood sample is a supernatant after centrifugation,
   the supernatant is obtained by:
   centrifuging a collection device containing a collected blood sample and an anticoagulant at high speed to obtain the supernatant.

5. The method according to claim 2, wherein the isolating of exosomes is conducted by using a magnetic-bead separation method, an affinity separation method or a combination thereof.

6. The method according to claim 2, wherein the isolating of exosomes is conducted by sorting or capturing with a specific antibody against at least one antigen selected from PLAP, CD9, and CD81.

7. The method according to claim 5, wherein the magnetic-bead separation method is conducted by isolating with a magnetic bead conjugated with a CD9 antibody or a PLAPl antibody on the surface.

8. The method according to claim 1, wherein in (iii), the presence of fetal-derived DNA in the exosomal DNA is detected by at least one of techniques selected from PCR amplification technique, sequence-specific probe capturing technology and high-throughput sequencing technology.

9. The method according to claim 1, wherein the isolating is conducted by using a magnetic-bead separation method, and the magnetic-bead separation method is conducted by isolating with a magnetic bead conjugated with a CD9 antibody or a PLAPI antibody on the surface.

10. The method according to claim 1, wherein the detecting comprises determining the number and/or sequence information of fetal-derived Y chromosomes; or the detecting comprises determining fetal-derived DNA fraction.

11. The method according to claim 1, further comprising: constructing a sequencing library for the exosomal DNA to obtain an exosomal DNA sequencing library.

12. The method according to claim 11, further comprising: subjecting the exosomal DNA sequencing library to high-throughput sequencing, so as to obtain information of the exosomal DNA.

13. A method for non-invasive prenatal gene detection, comprising:

(a) performing the steps (i) and (ii) according to claim 1 to obtain exosomal DNA, wherein the exosomal DNA comprises fetal-derived DNA;

(b) detecting the presence of fetal-derived DNA in the exosomal DNA; and (c) generating a gene detection result based on information obtained in (b).

14. The method according to claim 13, wherein the gene detection comprises:

determination of fetal-derived DNA fraction, determination of fetal sex, detection of autosomal genetic disease, detection of sex chromosome-linked disease, determination of RhD blood type or detection of chromosome aneuploidy.

15. The method according to claim 14, wherein the detection of chromosomal aneuploidy comprises detection of trisomy 21, trisomy 18 or trisomy 13.

16. A method for non-invasive prenatal gene detection, comprising:

(a) performing the method according to claim 12 to obtain information of exosomal DNA; and (b) generating a gene detection result based on the information obtained in (a);

wherein the exosomal DNA comprises fetal-derived DNA.

17. The method according to claim 16, wherein the gene detection comprises:

determination of fetal-derived DNA fraction, determination of fetal sex, detection of autosomal genetic disease, detection of sex chromosome-linked disease, determination of RhD blood type or detection of chromosome aneuploidy.

18. The method according to claim 17, wherein the detection of chromosomal aneuploidy comprises detection of trisomy 21, trisomy 18 or trisomy 13.

* * * * *